United States Patent [19]

Kuhla et al.

[11] Patent Number: 4,722,925
[45] Date of Patent: Feb. 2, 1988

[54] BICYCLIC BENZO-OXY HETEROCYCLIC ETHERS AND THIOETHERS PHARMACEUTICAL COMPOSITIONS AND USE

[75] Inventors: Donald E. Kuhla, Doylestown; Henry F. Campbell, Lansdale; William L. Studt, Harleysville; Kent W. Neuenschwander, Ambler, all of Pa.

[73] Assignee: Rorer Pharmaceutical Corporation, Fort Washington, Pa.

[21] Appl. No.: 21,147

[22] Filed: Mar. 3, 1987

Related U.S. Application Data

[62] Division of Ser. No. 881,122, Jul. 2, 1986, Pat. No. 4,668,673, which is a division of Ser. No. 664,063, Oct. 23, 1984, Pat. No. 4,612,309.

[51] Int. Cl.$^4$ .................. A61K 31/34; A61K 31/535; C07D 307/82; C07D 413/04
[52] U.S. Cl. ..................... 514/212; 514/222; 514/228; 514/232; 514/237; 514/320; 514/397; 514/406; 514/422; 514/459; 514/469; 514/470; 540/596; 544/58.7; 544/151; 544/153; 546/196; 548/336; 548/374; 548/525; 549/404; 549/407; 549/467
[58] Field of Search ............... 540/596; 544/58.7, 151, 544/153; 546/196; 548/336, 374, 525; 549/404, 407, 467; 514/212, 222, 228, 232, 237, 320, 397, 406, 422, 459, 469, 470

[56] References Cited

U.S. PATENT DOCUMENTS 4,500,543  2/1985  Debernardis et al. .............. 549/467
4,656,180  4/1987  Postius ................................ 514/212

*Primary Examiner*—Robert W. Ramsuer
*Attorney, Agent, or Firm*—James A. Nicholson; Alexis Barron; Martin F. Savitzky

[57] ABSTRACT

A class of bicyclic benzo-oxy heterocyclic ether and thioether compounds exhibiting pharmacological activity, including anti-secretory and anti-ulcerogenic activity, pharmaceutical compositions comprising these compounds, and methods for the treatment of gastrointestinal hyperacidity and ulcerogenic disorders in mammals using said compositions.

24 Claims, No Drawings

BICYCLIC BENZO-OXY HETEROCYCLIC ETHERS AND THIOETHERS PHARMACEUTICAL COMPOSITIONS AND USE

This is a divisional of co-pending application Ser. No. 881,122 filed on July 2, 1986, now U.S. Pat. No. 4,668,673 which is a divisional of application Ser. No. 664,063 filed Oct. 23, 1984, now U.S. Pat. No. 4,612,309.

FIELD OF THE INVENTION

This invention relates to novel bicyclic benzo-oxy heterocyclic compounds useful as $H_2$-antagonist agents in the treatment of ulcerogenic, hypersecretory and other gastrointestinal disorders. This invention also relates to methods for the treatment of gastrointestinal disorders, pharmaceutical compositions, and processes for the preparation of chemical compounds.

Gastrointestinal hyperacid secretion, stomach and intestinal ulceration, and gastritis are major gastrointestinal disorders observed in the general adult populations of industrialized societies. Many factors, including the production of excess gastric acid and the weakening of the lining of the stomach and gastrointestinal tract against such acid, are implicated as causes of these disorders.

Reported Developments

Traditional treatment of gastrointestinal disorders has involved the administration of antacids to neutralize the excess gastric acid and the administration of anti-secretory drugs which generally reduce the production of all gastric secretions.

In the last few years, the treatment of gastrointestinal disorders such as peptic ulcer has changed to include the use of anti-secretory drugs which selectively block the production of gastric acid. These drugs are believed to interfere with the body's physiological pathway responsible for the production of gastric acid by blocking the action of histamine. Histamine production is induced in the body by a number of stimuli, including stress, allergic reaction, etc., and acts to increase gastric secretion, dilate blood vessels and stimulate smooth muscle tissue. Histamine is believed to function by way of interaction with histamine receptors in the body. The subdivision of these receptors into two groups, the $H_1$- and $H_2$-receptors, was proposed by Ash and Schild (Brit. J. Pharmacol. Chemother, 1966, 27, 427) and Black et al (Nature 1972, 236, 385). The $H_1$-receptor is involved in the bronchial and gastrointestinal smooth muscle stimulative action of histamine. Drugs which block this action are labelled "antihistamines" (e.g. mepyramine).

Black et al, cited above, described the group of substances which act at histamine receptors other than the $H_1$-receptor as the $H_2$-receptors. Blocking the action of histamine at the $H_2$-receptors will selectively block histamine's stimulative action on gastric acid secretion and heart rate. Burimamide was the first clinically effective $H_2$-receptor antagonist inhibiting gastric secretion in man; but Burimamide's oral absorptivity is poor. Subsequent studies developed the orally active Metiamide, the side effects of which limited clinical use, and Cimetidine which has been marketed as an anti-ulcer drug. A number of classes of heterocyclic chemical compounds have been reported as $H_2$-receptor antagonists, for example, those disclosed in U.S. Pat. Nos. 4,104,381, 4,279,819, 4,323,566, 4,390,701, 4,395,553, and British published patent applications GB Nos. 2067987A and 2047238A, and EPO publication No. 0081955A2, the disclosures of which are incorporated by reference.

Another method for the prevention or treatment of gastric ulcer comprises the use of drugs which neither neutralize nor inhibit the secretion of gastric acid. These drugs constitute a class of anti-ulcer compounds which function to enhance the normal defense mechanisms of the body, rather than to reduce normal body secretions, and are described as "cytoprotective" agents. It has been proposed that such agents act to strengthen the mucosal lining of the gastrointestinal system by one or more mechanisms, thereby preventing any damage which could result from the action of strong gastric acid. Prostaglandins have been implicated in the mechanism of cytoprotection by a number of workers in the field. See, the discussion of cytoprotection in Robert, Andre, "Prostaglandins and Digestive Diseases", *Advances in Prostaglandin and Thromboxane Research* Vol. 8 (Raven Press, N.Y. 1980), and Robert et al, "Cytoprotection by Prostaglandins in Rats", *Gastroenterology*, 77, 433–443 (1979), hereby incorporated by reference. Drugs, other than prostaglandins, which exhibit cytoprotective activity include carbenoxolone sodium, reported to exhibit undesirable side effects, such as edema, diastolic hypertension or hypokalemia, and the thiazol-2-yl-carbamoylcarboxylic acids, esters and imides described in U.S. Pat. No. 4,321,372.

Bicyclic carbocyclic and nitrogen-containing heterocyclic alkylene ether and alkylene thioether compounds exhibiting anti-secretory, $H_2$-receptor antagonist, anti-ulcer and cytoprotective activity have been reported in copending U.S. application Ser. Nos.: 489,702; 400,350; 595,564; 489,814; and 604,988; all of which are assigned to the same assignee as the present application.

SUMMARY OF THE INVENTION

The present invention relates to a class of aromatic oxygen-containing bicyclic compounds which are substituted by an amino group and either an amino alkyleneoxy or an amino alkylene mercaptyl group, and which exhibit anti-secretory, $H_2$-antagonist anti-ulcer and cytoprotective activity.

This invention more particularly relates to a class of compounds according to Formula I

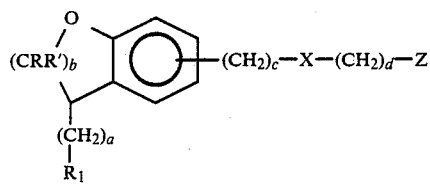

wherein:
a is 0, 1 or 2;
b is 1 or 2;
c is 0 or 1;
d is 2, 3 or 4;
X is oxygen, sulfur,

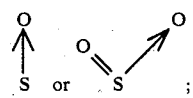

Z is —NHR$_4$, CN or $$\begin{array}{c} \text{N}-\text{SO}_2\text{NH}_2 \\ \| \\ -\text{C}-\text{NH}_2 \end{array} ;$$

R and R' are each independently H or alkyl;
$R_1$ is $-NR_2R_3$ or $$\begin{array}{c} \text{NR}_6 \\ \| \\ -\text{C}-\text{NR}_2\text{R}_3; \end{array}$$

$R_2$ and $R_3$ are each independently H or alkyl, or both together are alkylene or alkylidinyl and with the nitrogen to which they are attached form a 5, 6, or 7-membered ring which may include one to three additional hetero atoms of N, O or S;

$R_4$ is selected from the group consisting of H,

[structures: $-\overset{\text{N}-\text{CN}}{\underset{\|}{\text{C}}}-\text{NH}-\text{R}_5$, $-\overset{\text{CH}-\text{NO}_2}{\underset{\|}{\text{C}}}-\text{NH}-\text{R}_5$, $-\overset{\text{N}-\text{CN}}{\underset{\|}{\text{C}}}-\text{S}-\text{R}_5$, thiadiazole-NHR_5 structure,]

[additional heterocyclic structures with $R_5$, $R_7$, $R_{13}$, $R_{14}$, $R_{15}$ substituents]

; or $R_5$ is H or lower alkyl;
$R_6$ is H or lower alkyl or $R_6$ and $R_2$ together are ethylene or propylene and form a 5- or 6-membered ring together with the nitrogens to which they are attached;
$R_7$ is $NR_8R_9$, lower alkyl, aryl, arloweralkyl, lower alkoxy, aryloxy, aryloxy lower alkyl, hydroxy lower alkyl, lower alkoxy lower alkyl, halo, hydroxy, mercapto or lower alkyl mercapto;
$R_8$ is hydrogen, loweralkyl, lower alkenyl or arloweralkyl;
$R_9$ is hydrogen, $COR_{10}$, $SO_2R_{11}$ or $$\begin{array}{c} \text{X} \\ \| \\ \text{C}-\text{NHR}_{12}; \end{array}$$

$R_{10}$ is hydrogen, loweralkyl, aryl, arloweralkyl, loweralkoxy, heteroaryl, or monocyclic heteroarylalkyl;
$R_{11}$ is lower alkyl or aryl;
$R_{12}$ is hydrogen, lower alkyl, cycloloweralkyl, aryl or arloweralkyl;
$R_{13}$ is halo, amino, nitro, cyano, hydroxy, lower alkyl, lower alkoxy, lower alkanoyl, cycloloweralkyl, mono- or dilower alkyl amino, lower alkanoyl, lower alkanoyl amino, haloloweralkyl, aryl, mercapto, loweralkoxy carbonyl, carboxy, loweralkylthio, loweralkylsulfonyl, sulfamoyl, or lower alkyl sulfamoyl;
$R_{14}$ is $SO_2$, SO, S or $C=O$; and
$R_{15}$ is alkaryl;
or a pharmaceutically acceptable salt thereof.

This invention also relates to methods for the treatment and prevention of gastrointestinal hyperacidity and ulcerogenic disorders in humans and other mammals comprising administering to a patient an effective amount of a compound within the scope of Formula I, and processes for the preparation of the compounds and intermediates leading up to the compounds within the scope of Formula I.

DETAILED DESCRIPTION OF THE INVENTION

Preferred classes of compounds according to this invention are described by Formulae II and III.

[Formula II: phenyl ring with R, R', $(CH_2)_a$, $R_1$, and $(CH_2)_c-X-(CH_2)_d-Z$ substituents]

II

[Formula III: chroman ring with $(CH_2)_a$, $R_1$, and $(CH_2)_c-X-(CH_2)_d-Z$ substituents]

III wherein:
a, c, d, X, Z, R, R' and $R_1$ and $R_{15}$ are as defined above.

A preferred group of Z substituents comprise $NHR_4$, where $R_4$ may be one of the following radicals:

[structures: $-\overset{\text{N}-\text{CN}}{\underset{\|}{\text{C}}}-\text{NH}-\text{R}_5$, $-\overset{\text{CH}-\text{NO}_2}{\underset{\|}{\text{C}}}-\text{NH}-\text{R}_5$, $-\overset{\text{N}-\text{CN}}{\underset{\|}{\text{C}}}-\text{S}-\text{R}_5$, thiadiazole-NH-R_5 structure,]

[additional heterocyclic structures with $R_5$, $R_{15}$, $NH_2$ substituents]

-continued

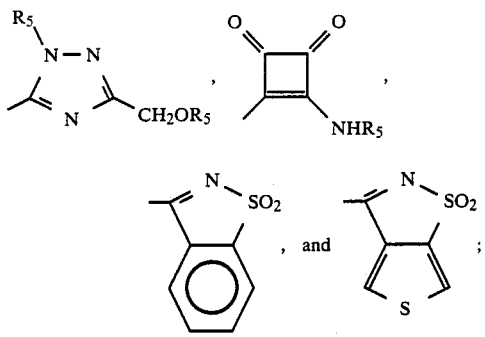

wherein:
$R_5$ is H or lower alkyl; and
$R_{15}$ is alkarylalkyl;

A preferred class of compounds of the present invention are compounds within the scope of either Formulae II or III,
wherein:
c is 0;
d is 3;
X is oxygen; and
Z is $NHR_4$.

Another class of compounds of particular interest are within the scope of Formulae II or III, wherein:
c is 1;
d is 2;
X is sulfur; and
Z is $NHR_4$.

Other classes of the compounds of particular interest are compounds within the scope of Formulae II or III, wherein:
a is 0; and/or
$R_1$ is 1-piperidyl, 1-pyrrolidinyl, 1 morpholinyl or 1-azepinyl.

A most preferred class of compounds of the present invention comprises compounds of Formulae II or III wherein the $-(CH_2)_c-X-(CH_2)_d-Z$ group is attached to the phenylene ring in the position ortho or para to the endocyclic oxygen atom.

A special embodiment of the present invention includes compounds within the scope of Formula IV:

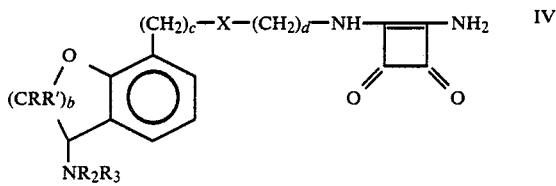

wherein:
b is 1 or 2;
c is 0 or 1;
d is 2, 3, or 4;
X is oxygen or sulfur;
R and R' are each independently H or lower alkyl;
$R_2$ and $R_3$ are together alkylene or alkylidinyl and with the nitrogen to which they are attached form a 5, 6 or 7 membered heterocyclic ring which may include one to three additional hetero atoms of N, O or S;
or a pharmaceutically acceptable salt thereof.

The compounds of Formulae I to IV may also form hydrates and exhibit tautomerism, and the above formulae are intended to encompass all hydrates and tautomers, as well as any diastereomers and optical enantiomers.

As employed above and throughout the disclosure, the following terms, unless otherwise indicated, shall be understood to have the following meanings:

"Alkyl" means an aliphatic group. "Lower alkyl" is an alkyl group having 1 to about 6 carbon atoms and is preferred. Examples of lower alkyl groups are methyl, ethyl, n-propyl, isopropyl, butyl, sec-butyl, tert-butyl, n-pentyl, isopentyl, neopentyl and n-hexyl.

"Cycloalkyl" means a cyclic aliphatic group. "Cycloloweralkyl" groups are preferred and comprise about 3 to about 7 carbon atoms.

"Heterocycle" means a hetero atom-containing ring. Preferred heterocycles in the context of the present invention are azaheterocycles of the formula

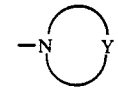

where Y is alkylene or alkylidinyl having from one to six carbon atoms, and may include one to three atoms of N, O or S. Exemplary azaheterocycles include piperidinyl, pyrrolidinyl, morpholinyl, azepinyl, pyrrolyl, imidazolyl, pyrazolyl, and thiamorpholinyl.

"Lower alkanoyl" means an acyl derivative of a lower alkanoic acid such as acetyl and propionyl.

"Heteroaryl" means a five or six membered monocyclic aromatic ring which may contain one or more heteroatoms of nitrogen, oxygen or sulfur, including furyl, pyridyl, thiazolyl, imidizolyl, oxazolyl, isooxazolyl, isothiazolyl or thienyl.

"Heteroarylalkyl" means an alkyl group substituted with a heteroaryl group as defined above. Heteroaryl lower alkyl groups are preferred.

"Aryl" means an aromatic hydrocarbon radical group such as phenyl or toluyl, and includes phenyl or toluyl substituted by one or more substituent groups including lower alkyl, halo, carboxyl, amino, lower alkylamino, amido, hydroxyl, nitro, cyano, or lower alkylsulfonyl. Phenyl and toluyl are preferred aryl groups.

"Arloweralkyl" means a lower alkyl group substituted with an aryl group as defined above.

"Alkarylalkyl" means an alkyl group substituted with

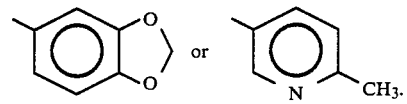

Methylene groups are the preferred alkyl group in the alkaryl radical.

"Aryloxy" means an oxy radical substituted with an aryl group as defined above.

"Aryloxy lower alkyl" means an aryl lower alkyl ether radical.

"Sulfamyl" is the radical of the formula $NH_2-SO_2-$.

"Amine substituent" means a radical group of the formula $-NR_3R_4$ wherein $R_3$ and $R_4$ are as defined above.

The compounds of this invention may be prepared by one of the following general synthetic schemes.

Compounds within the scope of Formula I, where b is 1, can be prepared starting from the appropriately substituted benzofuranones, which are either commercially available or can be prepared from commercially available substituted benzenes by methods known in the art.

Compounds within the scope of Formula I where b is 2, can be prepared starting from appropriately substituted benzopyranones which are commercially available or which can be prepared by methods known in the literature.

When the bicyclic benzo-oxy portion of the compound is directly attached to the X component depicted in Formula I, the compounds can be prepared from a bicyclic phenolic (or phenylmercaptan) intermediate, a benzopyranone example of which is Formula V below.

Scheme I

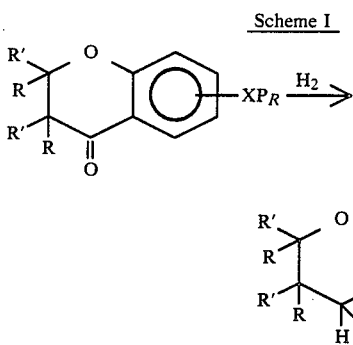

The benzopyranone starting material is reduced to the dihydrobenzopyranol intermediate VI as shown in Scheme I above. Catalytic hydrogenation, utilizing a noble metal catalyst under at atmosphere of hydrogen, is the preferred reduction method, although other reduction means may also be utilized, such as reducing using a hydride reagent such as a borohydride or aluminum hydride. The reduction results in the formation of an assymmetric center in the compound of Formula VI. The selectivity of this reaction may be influenced by the use of an optically active catalyst or reaction media, and thereby increase or decrease the percentage of either the R or S orientation of the assymmetric center. The racemic mixture can be resolved either as the alcohol intermediate, as the amino or methylene amino intermediates or as the final product, discussed in more detail below.

The next step in the present process comprises the conversion of the hydroxy intermediate of Formula VI into an amino group. This may be accomplished by transforming the hydroxyl group into a good leaving group and displacing it with a nitrogen nucleophile. A preferred reaction sequence comprises the transformation of the hydroxy group into a mesylate or tosylate, under standard conditions, by reacting the hydroxyl compound with either methyl- or toluene-sulfonyl chloride in the presence of a non-nucleophilic base, for example, a tertiary amine. Subsequent treatment of the sulfonyl addition product with a secondary amine such as methylamine, ethylamine, piperidine, morpholine, or the like, results in the desired amine product of Formula VII shown in Scheme II below.

Scheme II

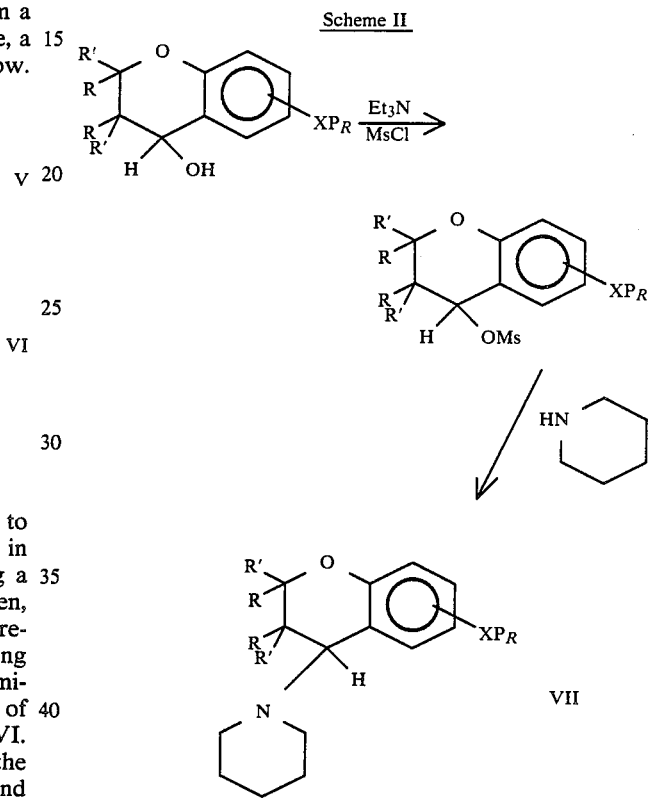

An alternate route to effecting the amine displacement and result in compounds of Formula VII involves the reduction of the bicyclic ketone of Formula V followed by the halogenation of the resulting hydroxy compound and the substitution of the desired amino group for the halo group. (See Scheme III below.)

Scheme III

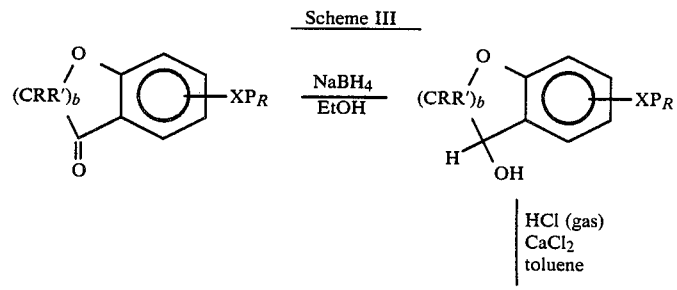

Scheme III

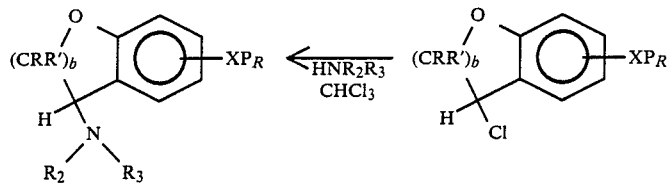

Compounds within the scope of Formula I, where "a" is greater than zero, may be prepared by the addition of one or more carbon units at the keto-position of the benzopyranone or benzofuranone starting material as exemplified in Scheme IV, below.

step conversion of the ketone to the cyano derivative, see O. H. Oldenziel et.al., J. Org. Chem., Vol. 42, No. 19, 3114–3117 (1977). The most preferred base is tert-butoxide in a non-polar aprotic solvent such as dimethylsulfoxide or HMPT. The resulting cyano compound

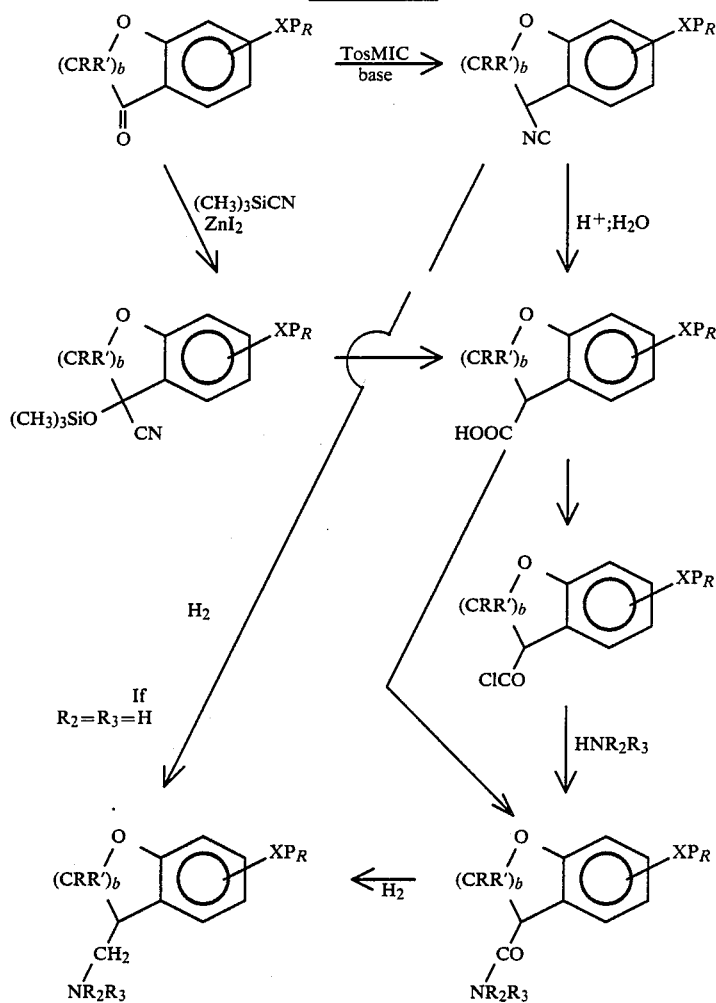

Treatment of the bicyclic ketone with trimethylsilylcyanide and zinc iodide forms the cyano trimethylsiloxy adduct. Treatment of the resulting siloxy compound with a mixture of a Lewis acid such as tin$^{II}$ chloride and a concentrated halogenic acid such as conc. HCl in glacial acetic acid results in the formation of the carboxylic acid derivative. (See, J. L. Belletire et.al, Synth. Commun. 12, No. 10, 763–70 (1982)). An alternative pathway to the carboxylic acid compound which also provides the pathway to amido and amidino derivatives is effected by the use of tosylmethylisocyanide in the presence of base. For a complete discussion of the onemay be hydrolyzed to the acid by means of aqueous base, for example, aqueous sodium hydroxide, or it may be hydrolyzed to the carbamoyl derivative by acidic means including, for example, $BF_3$ in glacial acetic acid or aqueous hydrochloric acid.

The mono- or di-substituted amide may be formed by the reaction of the acyl chloride, prepared by treating the acid with $SOCl_2$ with a primary or secondary amine, i.e., $HNR_2R_3$. The amide may also be formed directly by a condensation reaction of the acid and amine or through the ester by amide-ester interchange.

Reduction of the amide results in the methylene amine. A hydride reducing agent such as LiAlH$_4$ in diethyl ether or tetrahydrofuran is preferred. Other reagents which may be used include LiAlH$_4$ and AlCl$_3$ prepared via the carboxylic acid intermediate of Formula VIII by one or more alkylene chain extension reactions as shown, for example, in Scheme VI, below.

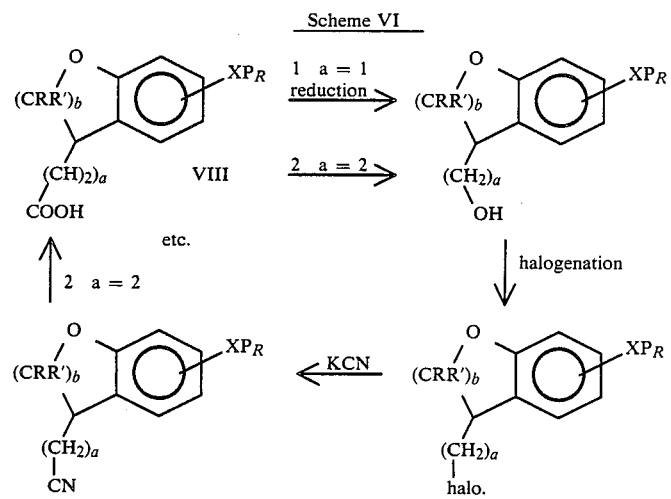

Scheme VI in an ether solvent, boron tetrafluoride etherate in methylene chloride followed by sodium borohydride in ethanol, and diborane in tetrahydrofuran. These reagents may also be used to obtain the amine directly from the cyano intermediate. The preferred reagent is LiAlH$_4$. The amine obtained from the reduction of the nitrile may be alkylated to form the mono-, di- or cyclized derivative using the appropriate alkylating agent, such as an alkyl iodide, alkyl triflate or 1,4-dihalo-, 1,5-dihalo-, or 1,6-dihalo-alkyl compound. The pyrrolidinyl, 1-piperidinyl, morpholinyl and azepinyl compounds may be prepared by alkyating the amine with the appropriate reagents, for example, 1,4-dibromobutane or 1,5-dibromopentane.

The amidino derivatives may be prepared from the cyano intermediate as shown in Scheme V below. Treatment with anhydrous ethanolic hydrochloric acid forms the ethoxy iminium salt which forms the amidine upon treatment with a primary or secondary amine.

Reduction of the carboxylic acid, shown in Scheme VI, with a hydride such as diborane is followed by the conversion of the resultant hydroxy compound into the halo derivative with a halogenation reagent such as SOCl$_2$ or PBr$_3$. The chain-extended cyano compound is generated by treatment of the halo derivative with cyanide and either can be converted into the amide, amine or guanidine as described above, or the chain extension process can be continued by regenerating via the carboxylic acid.

Another process for the preparation of compounds within Formula I wherein a is greater than zero, comprises the formation of spiro cyclic ether intermediate by the reaction of an ylid reagent with a cyclic ketone starting material. (See Scheme VII, below). Rupture of the oxygen containing ring is effected with a nucleophilic nitrogen reagent H—NR$_2$R$_3$, followed by removal of the tertiary hydroxy group by dehydration. Hydrogenation of the unsaturated product is followed by elaboration of the phenolic or phenyl mercaptan side chain as discussed herein below.

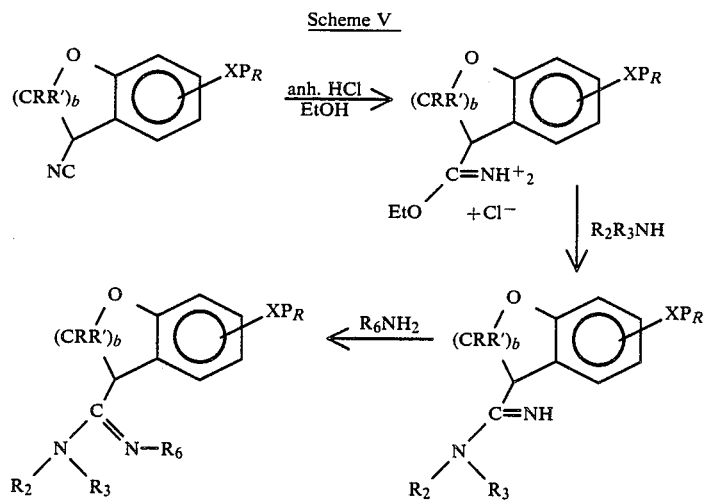

Scheme V

The ethylene amino and higher alkylene amino compounds, where a$\geq$2, according to Formula I, may be Scheme VII

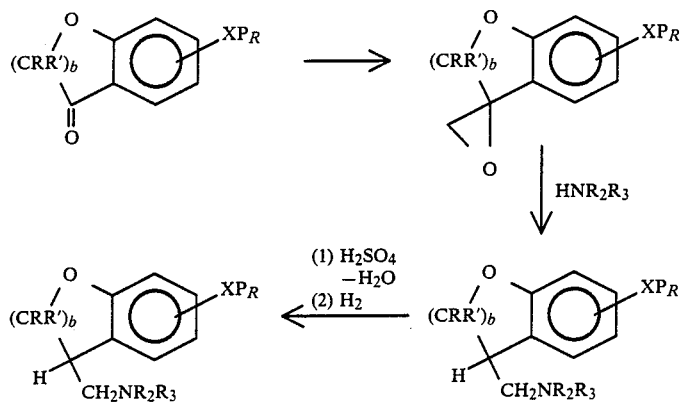

The protecting group, $P_R$, in the above formulae, may be methyl, benzyl or N-phthalimido alkyl. If the protecting group is chosen to be other than N-phthalimido alkyl, the protecting group is removed according to methods known in the art. If the protecting group is N-phthalimido alkyl, then it can remain on the synthetic intermediate throughout the foregoing reactions and used as the source of the alkylene ether or alkylene thioether chain in subsequent reaction steps.

The formation of the ether linkage from the phenolic compound of Formula IX below, is accomplished by treating the phenolic compound with a protected N-propylbromide in the presence of a base such as sodium methoxide, potassium t-butoxide or potassium carbonate. Ether coupling reagents other than a base and a bromide may also be used. (See Scheme VIII, below)

Scheme VIII

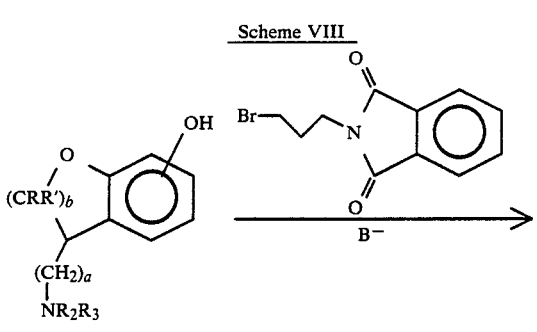

IX

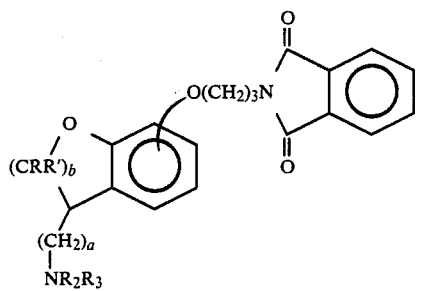

The nitrogen protecting group is preferably phthalimido but can be any protecting group insensitive to the ether formation reaction conditions, such as a base insensitive group.

The amine compound is obtained by the removal of the protecting group, for example, the phthalimido group is removed with hydrazine hydrate. (See Scheme IX, below)

Scheme IX

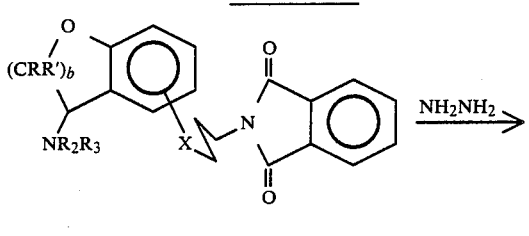

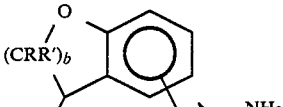

An alternate route for the formation of the ether linkage from Formula IX involves the base catalyzed reaction of the phenolic compound with an α,ω-dihaloalkyl reagent followed by the nucleophilic displacement of the α-halo substituent by azide and the reduction of the azido functionality to the amine. Scheme X depicts the alternate "azide" route.

Scheme X

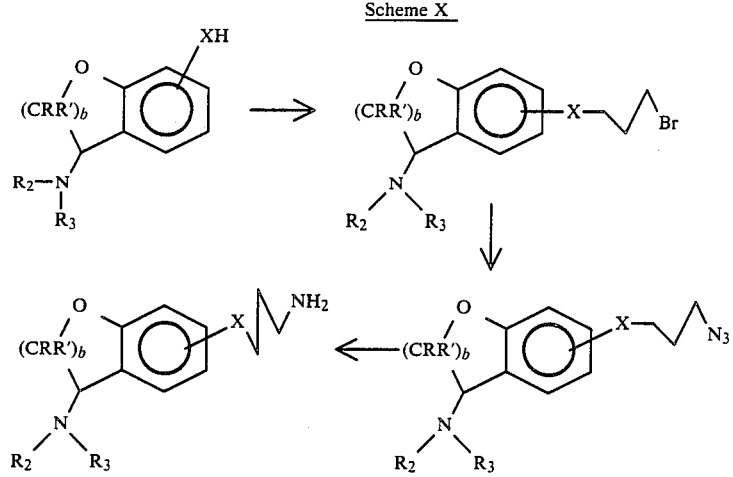

Compounds within the scope of Formula I and having a methyleneoxy or methylenethioxy substituent (d=1) on the phenyl portion of the compound may be prepared by one of the reaction sequences described below.

The methyleneoxy or methylenethio ether may be prepared from the coupling of a 2-bromoethylene phthalimide in the presence of base or 2-thioethylamine, respectively, with the methylene hydroxy compound. Scheme XI illustrates the formation of the methylene thioether.

Scheme XI

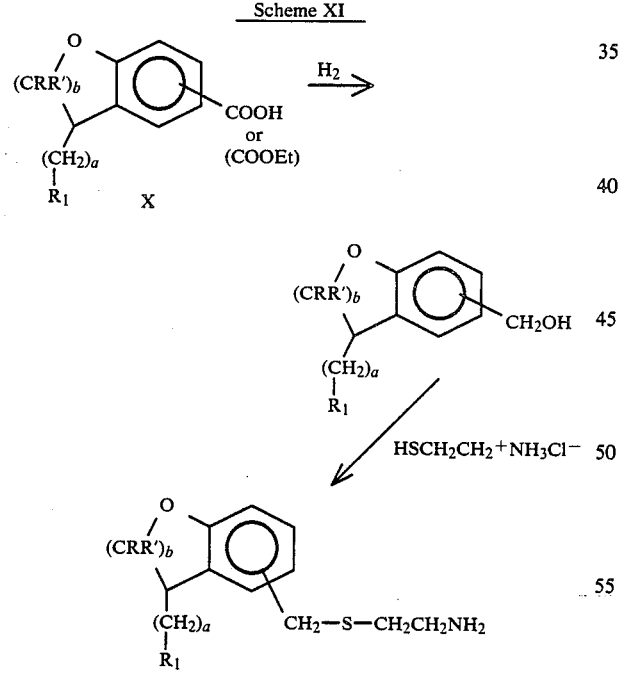

The methylene oxy compound may be obtained by the reduction of a carboxylic acid or ester precursor such as the compound of Formula X above. The reduction may be conducted by hydrogenation over a rhenium catalyst, by a hydride in the presence of a Lewis acid or by acidic electrolysis and, depending on the choice of conditions, may take place before or after the formation of the amine. If the reduction to the methylene hydroxy compound occurs after the formation of the amine, the carboxylic acid intermediate is protected in the form of the ester.

The addition of the terminal $R_4$ group comprises treating the amine intermediate with an $R_4$ end group precursor unit including those groups listed in Scheme XII below. The preparation of the precursors of the $R_4$ groups shown in Scheme XII and the reaction conditions under which they are coupled to the primary amine are fully described in U.S. Pat. Nos. 4,104,381, 4,279,819, 4,323,566, 4,390,701, 4,395,553, and GB Nos. 2047238A, 2067987A, and EPO Publication No. 0081955A2, hereby incorporated by reference.

Additional $R_4$ groups include the thiatriazine group of the formula and the 5,5-bicyclic group of the formula

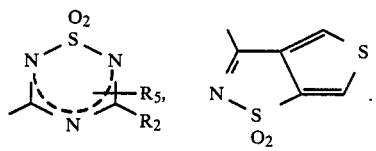

The preparation of the aforementioned thiatriazine precursor is disclosed in copending U.S. patent application Ser. No. 604,988, filed Apr. 27, 1984 and Attorney Docket No. 14,255-A, filed on the same day as the present application, both of which are assigned to the same assignee as the present application and are hereby incorporated by reference.

The 5,5-bicyclic group above may be prepared from the methyl mercaptyl derivative formed from the oxo-precursor, which is described in the *Journal of Organic Chemistry*, Volume 45, 617 (1980), hereby incorporated by reference. Upon treatment of the oxo-precursor with $P_2S_5$ in pyridine, the thione analog is formed, which in turn forms the methyl mercaptan compound on treatment with base and methyl iodide.

Scheme XII

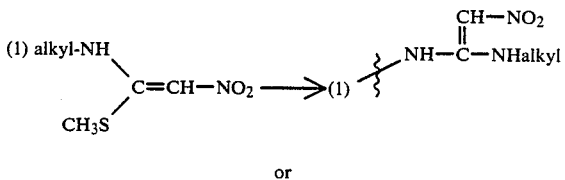

or

-continued
Scheme XII

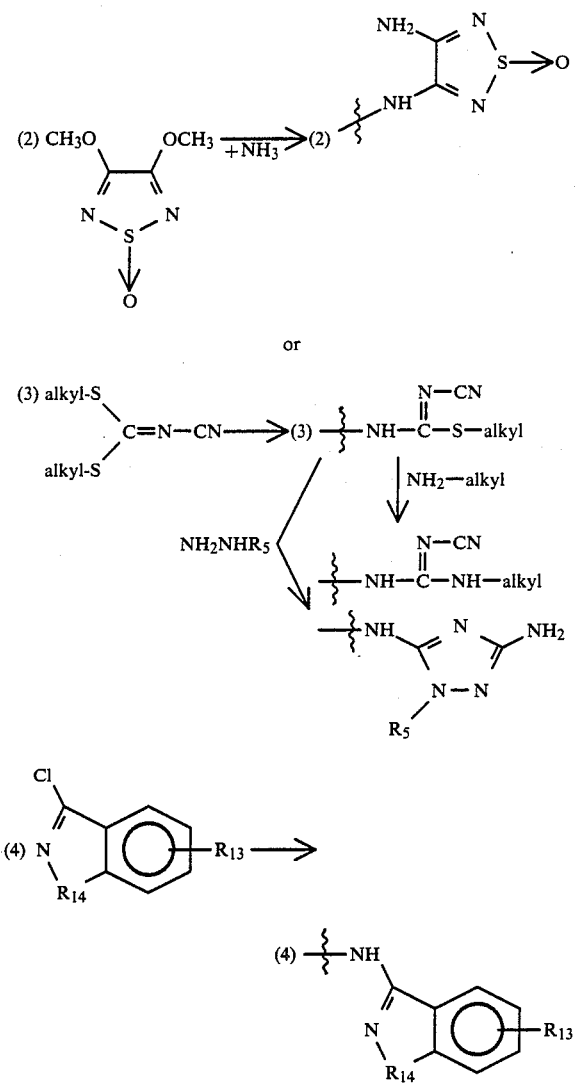

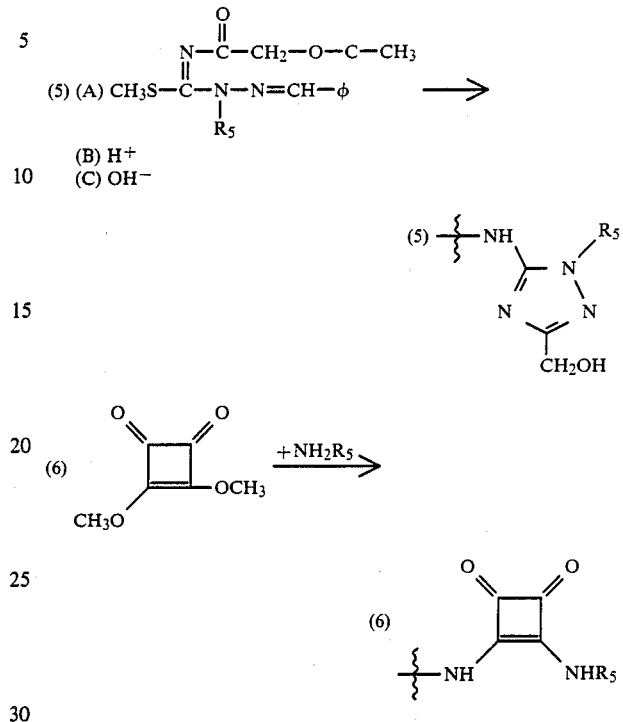

When Z is NH₂, CN or sulfamoyl amidine, the reaction sequence is slightly modified as shown below in Scheme XII for the benzopyranyl series. Reaction of the phenolic intermediate with a cyano-substituted alkylating agent such as 3-cyanopropylchloride in the presence of a base produces the cyano ether compound. Reduction of the cyano group with a hydride such as lithium aluminum hydride results in the amino compound. Treatment of the cyano compound with anhydrous methanolic HCl yields an imidate intermediate which is converted to the sulfonyl amidine by treatment with sulfamide in methanol. For a complete discussion of this preparatory sequence, see U.S. Pat. No. 4,283,408, incorporated herein by reference.

Scheme XIII

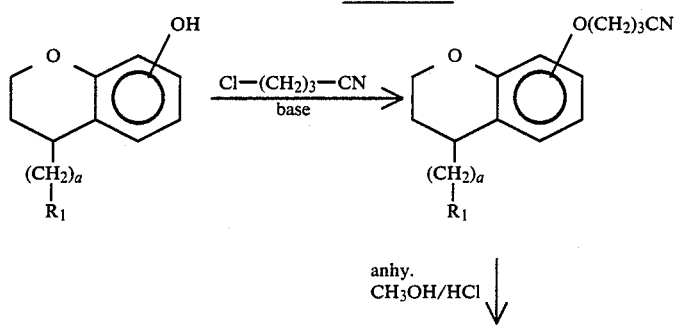

Scheme XIII

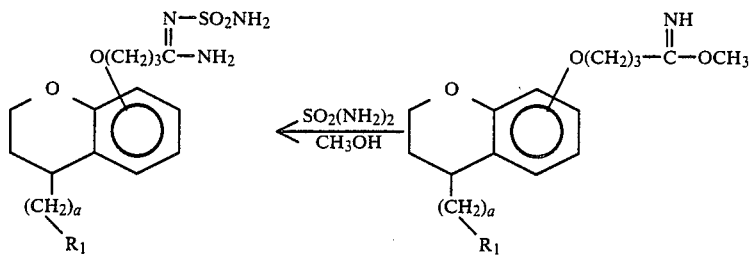

The analogous mercaptan compounds may be prepared by reacting a cyano mercaptan with the appropriate halo-methylene intermediate as shown in Scheme XIV below. The amino sulfonyl amidine compound is prepared by reaction sequences similar to those described above.

Scheme XIV

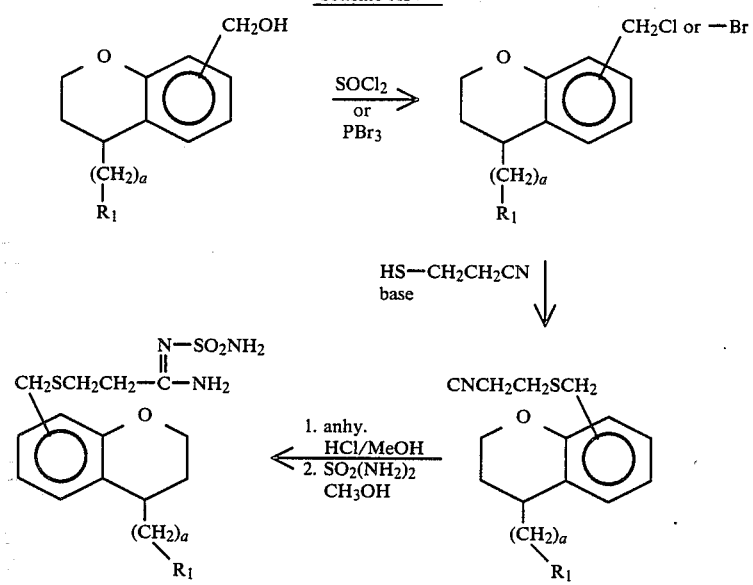

The compounds of this invention may be readily converted to their non-toxic acid addition salts by customary methods in the art. The non-toxic salts of this invention are those salts the acid component of which is pharmacologically acceptable in the intended dosages, including those prepared from inorganic acids such as hydrochloric acid, hydrobromic acid, sulfuric acid, nitric acid and phosphoric acid, and from organic acids such as methane sulfonic acid, benzenesulfonic acid, acetic acid, propionic acid, malic acid, oxalic acid, succinic acid, glycolic acid, lactic acid, salicyclic acid, benzoic acid, nicotinic acid, phtalic acid, stearic acid, oleic acid, abietic acid, etc.

The following are selected examples of the preparation of the compounds according to this invention.

EXAMPLE 1

THE PREPARATION OF 3-AMINO-5-[3-[6-[4-PIPERIDINO-2,3-DIHYDROBENZOPYRANYLOXY]]PROPYLAMINO]-1-METHYL-1H-1,2,4-TRIAZOLE

Step 1. 6-Methoxy-4-hydroxy-2,3-dihydrobenzopyran

A solution of 6-methoxy-4-benzopyranone (31.6 g), triethylamine (4.9 ml) and 10% palladium on carbon (3.16 g) in absolute ethanol (1.7 l) is stirred under an atmosphere of hydrogen for 19 hours. The reaction mixture is filtered and evaporated in vacuo yielding the desired hydrogenated product as a pale yellow liquid.

Step 2. 6-Methoxy-4-piperidino-2,3-dihydrobenzopyran

Methane sulfonyl chloride (14.9 ml) is added dropwise to a stirred solution of the product obtained in Step 1. (31.6 g) and triethylamine (29.3 ml) in methylene chloride (750 ml) cooled to 0° C. under nitrogen. The reaction mixture is stirred at RT for 2½ hours and cooled to 0° C. Piperidine (175 ml) is added to the cooled reaction mixture and the solution stirred at RT overnight. Sat'd aq. sodium bicarbonate is added to the solution and the mixture is stirred for 30 minutes. The organic layer is separated, washed with sat'd NaCl and dried. The solution is filtered and the filtrate evaporated in vacuo yielding the desired product as its hydrochloride salt.

Step 3. 6-Hydroxy-4-piperidino-2,3-dihydrobenzopyran

A solution of the product obtained in Step 2. (85 g), hydrobromic acid (630 ml) and acetic acid (630 ml) is refluxed for 3 hours. The reaction mixture is poured into crushed ice/H₂O and made alkaline. The resulting precipitate is taken up in methylene chloride and the methylene chloride solution washed with sat'd NaCl, dried, filtered and evaporated in vacuo. The residue is dissolved in methylene chloride and chromatographed on silica gel (300 g) eluting with ethyl acetate and hexane. The major fractions are combined, dissolved in methylene chloride and extracted with 5% aq. HCl. The acidic solution is made alkaline, extracted with methylene chloride, washed with water, dried, filtered and evaporated in vacuo yielding the desired product as a white solid.

Step 4.
6-(3-Bromopropoxy)-4-piperidino-2,3-dihydrobenzopyran

Crushed potassium hydroxide (1.15 g) and tetrabutyl ammonium chloride (0.61 g) are added to a solution of the product obtained in Step 3. (4.8 g) in 1,3-dibromopropane (21 ml). The reaction mixture is stirred under nitrogen at RT for 48 hours, diluted with diethyl ether, washed with water and extracted into 5% aq. HCl. The aqueous solution is washed with ether and made alkaline yielding a yellow oil which is taken up in ether, washed, dried, filtered and evaporated to give the desired product as an oil.

Step 5.
6-(3-Azopropoxy)-4-piperidino-2,3-dihydrobenzopyran

Sodium azide (0.81 g) is added to a solution of the product obtained in Step 4. (4.4 g) in aqueous ethanol (1:10). The reaction mixture is refluxed overnight, poured into water and extracted with methylene chloride. The organic extract is washed with water and sat'd NaCl, dried, filtered and evaporated in vacuo yielding the desired product as a liquid.

Step 6.
6-(3-Aminopropoxy)-4-piperidino-2,3-dihydrobenzopyran

A solution of the product obtained in Step 5. (3.8 g) in THF (15 ml) is added dropwise to a suspension of lithium aluminum hydride (0.6 g) in anhydrous diethyl ether (125 ml) under nitrogen. The reaction mixture is refluxed for 2 hours and quenched with 0.6 ml of $H_2O$, 0.6 ml of 15% sodium hydroxide and 1.8 ml $H_2O$. The resulting mixture is filtered, dried, filtered, and evaporated in vacuo yielding the desired product as a liquid.

Step 7.
3-Amino-5-[3-[6-[4-piperidino-2,3-dihydrobenzopyranyloxy]]-propylamino]-1-methyl-1H-1,2,4-triazole A neat mixture of N-cyano-1-methyl-2-(phenylmethylene) hydrazine carboximidthioic acid, methyl ether (1.88 g) and the product obtained in Step 6. (2.35 g) is heated at 72° C. in vacuo for 4 hours. The residue is dissolved in a mixture of 5% aq. HCl (30 ml) and acetone (20 ml). The aqueous solution is washed with ether and made basic thereby yielding a yellow oil which is taken up in ethyl acetate, washed with sat'd NaCl, dried and filtered and dried. The solution is concentrated and chromatographed on silica gel eluting with an ethyl acetate/hexane mixture. The purified fractions are combined and evaporated and the resulting white solid recrystallized from acetonitrile yielding the desired product, M.P.=140°–141° C.

EXAMPLE 2
THE PREPARATION OF 1-AMINO-2-[3-[6-(4-PIPERIDINO-2,3-DIHYDROBENZOPYRANYLOXY)]PROPYLAMINO]-CYCLOBUTENE-3,4-DIONE

A solution of 6-(3-aminopropyl)-4-piperidino-2,3-dihydrobenzopyran (2.3 g) in methanol (23 ml) is added dropwise to a stirred solution of 1,2-dimethoxycyclobutene-3,4-dione (1.12 g) in methanol (23 ml) under nitrogen and cooled to 0° C. The reaction mixture is stirred at 0° C. for 2½ hours. Anhydrous ammonia is bubbled through the solution for 10 minutes at 0° C. and the reaction mixture stirred at RT overnight. The resulting precipitate is filtered and washed with cold methanol and ether, yielding a yellow solid which is twice recrystallized from DMF affording the desired product as a white solid, M.P. 135°–137° C.

EXAMPLE 3
THE PREPARATION OF 3-AMINO-5-[3-[8-[4-PIPERIDINO-2,3-DIHYDROBENZOPYRANYLOXY]]-PROPYLAMINO]-1-METHYL-1H-1,2,4-TRIAZOLE

Step 1. 4-Hydroxy-8-methoxy-2,3-dihydrobenzopyran

A solution of 8-methoxy-4-benzopyranone (31.6 g), triethylamine (4.9 ml) and 10% palladium on carbon (3.1 g) in absolute ethanol (1.7 l) is stirred under an atmosphere of hydrogen (P=52 lbs.) overnight. The resulting solid is filtered, washed with diethyl ether and evaporated in vacuo yielding the desired product as a solid.

Step 2. 8-Methoxy-4-piperidino-2,3-dihydrobenzopyran

Methane sulfonyl chloride (14.9 ml) is added dropwise to a solution of the product obtained in Step 1. (31.6 g) and triethylamine (29.3 ml) in methylene chloride (750 ml) cooled to 0° C. under nitrogen. The reaction mixture is stirred for 1½ hours; piperidine (175 ml) is added and the reaction mixture is stirred under nitrogen overnight. The reaction mixture is washed with sat'd aq. sodium bicarbonate, sat'd NaCl, dried, filtered and evaporated in vacuo yielding the desired product as its hydrochloride salt.

Step 3. 8-Hydroxy-4-piperidino-2,3-dihydrobenzopyran

A mixture of hydrogen bromide (48%, 430 ml), the hydrochloride obtained in Step 2. (76 g) and glacial acetic acid (430 ml) is refluxed for 2 hours. The reaction mixture is poured into crushed ice/$H_2O$, made basic and taken up in methylene chloride. The organic phase is filtered, washed with water, dried, filtered and evaporated in vacuo. The residue is chromatographed on silica gel, eluting with ethyl acetate and hexane, affording the desired product as a clear liquid.

Step 4.
8-(3-Bromopropoxy)-4-piperidino-2,3-dihydrobenzopyran

Crushed potassium hydroxide (4.1 g) and tetrabutyl ammonium chloride (2.2 g) and $H_2O$ (5 ml) are added to a stirred mixture of the product obtained in Step 3. (17.2 g) and 1,3-dibromopropane (74.8 ml). The reaction mixture is stirred under nitrogen overnight, diluted with diethyl ether, and extracted with 5% aq. HCl. The acidic solution is washed with ether, sat'd NaCl, dried, filtered and evaporated in vacuo yielding the desired product as an oil.

Step 5.
8-(3-Azopropoxy)-4-piperidino-2,3-dihydrobenzopyran

Sodium azide (3.65 g) is added to a stirred solution of the product obtained in Step 4. (19.9 g) in aqueous ethanol (1:10) and the reaction mixture refluxed for 16 hours. The reaction mixture is filtered and evaporated in vacuo affording the desired product as an oil.

Step 6.
8-(3-Aminopropoxy)-4-piperidino-2,3-dihydrobenzopyran

A solution of the product obtained in Step 5. (17.5 g) in anhydrous THF (20 ml) is added dropwise to a suspension of lithium aluminum hydride (2.63 g) in anhydrous ether (720 ml). The reaction mixture is heated to reflux for 4 hours and quenched with 2.6 ml of $H_2O$, 2.6 ml of 15% aqueous NaOH and 7.8 ml of $H_2O$ and allowed to stir overnight. The mixture is filtered, dried, filtered and evaporated in vacuo affording a yellow oil which is chromatographed on silica gel eluting with a 1:1 mixture of methanol and ethyl acetate. The purified fractions are combined and evaporated affording the desired product.

Step 7.
3-Amino-5-[3-[8-[4-piperidino-2,3-dihydrobenzopyranyloxy]]-propylamino]-1-methyl-1H-1,2,4-triazole N-cyano-1-methyl-2-(phenylmethylene) hydrazine carboximidthioic acid, methyl ether (1.1 g) and the product obtained in Step 6. (1.4 g) are heated neat in vacuo at 70° C. for 4 hours and allowed to cool overnight. The mixture is stirred with a solution of acetone (30 ml) and 5% aq. HCl (45 ml), diluted with water and extracted with ether. The acidic solution is made basic, extracted with ethyl acetate and the organic layer washed with sat'd NaCl, dried, filtered and evaporated in vacuo. The residue is recrystallized from ethyl acetate yielding the desired product as a solid, M.P.=137°-138° C.

EXAMPLE 4

THE PREPARATION OF 3-AMINO-4-[3-[8-(4-PIPERIDINO-2,3-DIHYDROBENZOPYRANYLOXY)]PROPYLAMINO]-1,2,4-THIADIAZOLE MONOXIDE

A solution of 8-(3-aminopropoxy)-4-piperidino-2,3-dihydrobenzopyran (3.0 g) in methanol (43 ml) is added dropwise to a solution of 3,4-dimethoxy-1,2,5-thiadiazole monooxide (1.67 g) in methanol (180 ml) cooled to 0° C. under nitrogen. Anhydrous ammonia gas is bubbled into the solution for 10 minutes and the solution stirred at RT under nitrogen overnight. The reaction mixture is evaporated in vacuo and the residue recrystallized from ethanol and recrystallized from acetonitrile yielding the desired product, M.P.=184°-185° C.

EXAMPLE 5

THE PREPARATION OF 1-AMINO-2-[3-[8-(4-PIPERIDINO-2,3-DIHYDROBENZOPYRANYLOXY)]PROPYLAMINO]-CYCLOBUTENE-3,4-DIONE

A solution of 8-(3-aminopropoxy)-4-piperidino-2,3-dihydrobenzopyran (2.3 g) in methanol (23 ml) is added to a stirred solution of 1,2-dimethoxy-cyclobutene-3,4-dione (1.1 g) in methanol (23 ml) cooled to 0° C. under nitrogen. The reaction mixture is stirred for 10 minutes at 0° C., stirring continued at ambient temperature for 2½ hours and the reaction mixture recooled to 0° C. Anhydrous ammonia is bubbled into the reaction mixture for about 5 minutes and the reaction mixture stirred at RT under nitrogen overnight. The reaction mixture is filtered and the precipitate washed with methanol and diethyl ether, dried over potassium hydroxide in vacuo and the dried solid recrystallized from isopropanol yielding the desired product, M.P.=230°-232° C.

EXAMPLE 6

THE PREPARATION OF N-[3-[8-(1-PIPERIDINO-2,3-DIHYDROBENZOPYRANYLOXY)]PROPYL]-1,2-BENZOISOTHIAZOL-3-AMINO-1,1-DIOXIDE

A solution of 1,2-benzoisothiazol-3-chloro-1,1-dioxide (3.26 g) in chloroform (100 ml) is added over a period of 30 minutes to a stirred refluxing solution of 8-(3-aminopropoxy)-4-piperidino-2,3-dihydrobenzopyran (4.27 g) in chloroform (350 ml) under nitrogen. Refluxing is continued for an additional 30 minutes, than the reaction mixture is allowed to cool and evaporated in vacuo. The residue is dissolved in methanol, stirred with anhydrous sodium carbonate (4.3 g) for 15 minutes, filtered, evaporated and the residue taken up in a mixture of warm ethyl acetate/methanol (19:1). The solution is filtered, and the filtrate evaporated. The residue is twice recrystallized from ethyl acetate and methanol affording the desired product as a solid, M.P.=169°-171° C.

EXAMPLE 7

THE PREPARATION OF 3-HYDROXYMETHYL-5-[3-[8-(4-PIPERIDINO-2,3-DIHYDROBENZOPYRANYLOXY)]-PROPYLAMINO]-1-METHYL-1H-1,2,4-TRIAZOLE

Step 1. 1-Acetoxyacetyl-2-methyl-2-[phenylmethylene amino]-3-[3-[8-(4-piperidino-2,3-dihydrobenzopyranyloxy)]propyl]guanadine A neat mixture of methyl-N-[2-(acetyloxy)acetyl]-1-methyl-2-(phenylmethylene)hydrazine carboximidothioate (6.7 g) and 8-(3-aminopropoxy)-4-piperidino-2,3-dihydrobenzopyran (6.0 g) is heated to 65° C. under vacuum for about 18 hours. Boiling ethyl acetate (70 ml) is added to the heated mixture and the mixture stirred. The mixture is allowed to cool forming a precipitate which is filtered and the filtrate is concentrated in vacuo. The residue is triturated with ether forming a precipitate which is filtered. The filtrate is concentrated in vacuo yielding the desired product as an oil which is used in the next step without further purification.

Step 2.
3-Hydroxymethyl-5-[3-[8-(4-piperidino-2,3-dihydrobenzopyranyloxy)]propylamino]-1-methyl-1H-1,2,4-triazole A mixture of 1-acetoxyacetyl-2-methyl-2-[phenylmethyleneamino]-3-[3-[8-(4-piperidino-2,3-dihydrobenzopyranyloxy)]propyl]guanadine (1.6 g), aqueous HCl (12N, 70 ml) and absolute ethanol (15 ml) is stirred at RT for about 19 hours. The reaction mixture is washed with ether and the aqueous layer neutralized to pH7, treated with 2.2 ml of 4M KOH, diluted with ethanol (8 ml) and stirred for an additional 1½ hour. The reaction mixture is concentrated in vacuo and the aqueous concentrate extracted with ethyl acetate. The extract is dried, filtered and concentrated in vacuo. The residue is dissolved in methylene chloride and chromatographed (silica gel, 230-400 mesh) eluting with a mixture of methylene chloride and methanol, increasing the concentratio of methanol to 100%. The fractions are combined and concentrated in vacuo in an oil which is triturated with anhydrous ether. The resulting solid is filtered, dissolved in methanol and flash chromatographed on silica gel eluting the methanol. The purified fractions are combined and concentrated in vacuo to give an oil which is triturated with anhydrous ether. The precipitate is filtered, and dried yielding the desired product, M.P.=143°-145.5° C.

EXAMPLE 8

THE PREPARATION OF 3-AMINO-5-[3-[7-[3-PIPERIDINO-2,2-DIMETHYL-BENZOFURANYLOXY]]PROPYLAMINO]-1-METHYL-1H-1,2,4-TRIAZOLE

Step 1. 3-Isopropylcarbonyl-1,2,dimethoxybenzene

A solution of n-butyl lithium in hexane (278 ml) is added dropwise to a stirred solution of 1,2-dimethoxybenzene (81 ml) in diethyl ether (1,2 l) cooled to −10° C. under nitrogen. The reaction mixture is allowed to warm to RT and stirred under nitrogen for 6½ hours. The reaction mixture is cooled to −78° C. and isobutyric anhydride (154 ml) added. The reaction mixture is allowed to warm to RT, stirred under nitrogen overnight, washed with sat'd aq. sodium bicarbonate, sat'd NaCl and dried. The solution is filtered and evaporated in vacuo affording an oil which is distilled in vacuo yielding the desired product, B.P.=80°-150° C. (1 mm).

Step 2. 3-(2-Bromoisopropylcarbonyl)-1-methoxy-2-hydroxybenzene

Bromine (27 ml) is added to a stirred solution of the carbonyl product obtained in Step 1. (115 g) in methylene chloride (1.1 l) cooled to 0° C. The solution is stirred for 15 minutes and evaporated in vacuo. The residue is dissolved in methylene chloride (1.6 l) and cooled to 0° C. Aluminum chloride (72 g) is added portionwise to the stirred mixture and stirring is continued under nitrogen for about 48 hours at RT. The reaction mixture is poured into crushed ice/H₂O, the aqueous layer washed with methylene chloride and the combined organic fractions washed with sat'd aqueous NaCl, dried, filtered and evaporated in vacuo yielding the desired product as an oil.

Step 3. 7-Methoxy-2,2-dimethyl-3-benzofuranone

Sodium acetate hydrate (121 g) is added to a stirred solution of the product obtained in Step 2. (135 g) in absolute ethanol (2.5 l). The reaction mixture is refluxed for 5½ hours, allowed to cool, is evaporated in vacuo and the residue partitioned between ethyl acetate and sat'd aq. sodium bicarbonate. The layers are separated and the aqueous solution extracted with ethyl acetate. The organic phases are combined, washed with sat'd aq. sodium bicarbonate, sat'd aq. NaCl and dried, filtered and evaporated in vacuo. The residue is chromatographed on silica gel eluting with ethyl acetate and hexane (1:10). The purified fractions are combined and evaporated affording the desired product.

Step 4. 7-Methoxy-3-hydroxy-2,2-dimethylbenzofuran

An aqueous solution of sodium borohydride (8.2 g, 50 ml) is added to a stirred solution of the product obtained in Step 3. (41.8 g) in ethanol (1 l) and the mixture refluxed for 3 hours and evaporated in vacuo. The residue is taken up in water and toluene, the layers are separated and the organic phase washed, dried and evaporated in vacuo affording an oil which is dissolved in methylene chloride, dried, filtered and evaporated in vacuo. The residue is dissolved in ethyl acetate and chromatographed on silica gel affording the desired product as a white solid.

Step 5. 7-Methoxy-3-piperidino-2,2-dimethylbenzofuran

Triethylamine (29 ml) is added to a stirred solution of the product obtained in Step 4. (25.4 g) in methylene chloride (560 ml) at RT under nitrogen. Methanesulfonyl chloride (11.1 ml) is added dropwise to the mixture which is cooled to 0° C. The mixture is stirred for 3 hours at RT, cooled to 0° C., piperidine (128 ml) added and stirring continued at RT overnight. Sat'd aq. sodium bicarbonate is added to the mixture, the phases separated and the organic phase washed with sodium bicarbonate, sat'd NaCl, dried, filtered and evaporated in vacuo. The residue is dissolved in toluene and evaporated in vacuo affording the desired product as the hydrochloride salt.

Step 6. 7-Hydroxy-3-piperidino-2,2-dimethylbenzofuran

7-Methoxy-3-piperidino-2,2-dimethylbenzofuran (65.1 g) is added to a stirred mixture of glacial acetic acid (340 ml) and 48% HBr (340 ml) and the solution refluxed for 3 hours. The reaction mixture is poured into crushed ice/H₂O and brought to a pH=8-10. The alkaline reaction mixture is extracted with methylene chloride and the organic phase washed with water, dried, filtered and evaporated in vacuo. The residue is chromatographed on silica gel eluting with ethyl acetate/hexane (1:3) affording the desired product as a liquid.

Step 7. 7-(3-Bromopropoxy)-3-piperidino-2,2-dimethylbenzofuran

Potassium hydroxide (1.47 g), tetrabutyl ammonium chloride (0.77 g) and H₂O (1 ml) are added to a solution of the product obtained in Step 6. (6.6 g) in 1,3-dibromopropane (27 ml). The reaction mixture is stirred for 20 hours and diluted with diethyl ether and washed with 5% aq. HCl. The acidic solution is washed with ether and basified, affording an oil which is taken up in ether, washed with sat'd NaCl, dried, filtered and evaporated in vacuo affording the desired product as an oil.

Step 8. 7-(3-Azopropoxy)-3-piperidino-2,2-dimethylbenzofuran

Sodium azide (1.25 g) is added to a stirred solution of the product obtained in Step 7. (6.8 g ) in aqueous ethanol (1:10) and the reaction is stirred at reflux for 16 hours. The reaction mixture is diluted with water and extracted with methylene chloride. The organic phase is washed with sat'd NaCl, dried, filtered and evaporated in vacuo affording the desired product as an oil.

Step 9.
7-(3-Aminopropoxy)-3-piperidino-2,2-dimethylbenzofuran

A solution of the azo product obtained in Step 8. (6.1 g) in anhydrous THF (15 ml) is added dropwise to a stirred suspension of lithium aluminum hydride (0.8 g) in anhydrous diethyl ether (230 ml). The reaction mixture is refluxed for 24 hours and an additional 0.8 g of lithium aluminum hydride is added portionwise to the cooled solution. The reaction mixture is refluxed for an additional 8 hours and quenched with H$_2$O (1.6 ml), 15% aqueous NaOH (1.6 ml) and H$_2$O (4.8 ml). The reaction mixture is filtered and the filtrate evaporated in vacuo affording the desired product as a liquid which is used in the next step without further purification.

Step 10.
3-Amino-5-[3-[7-[3-piperidino-2,2-dimethylbenzofuranyloxy]]propylamino]-1-methyl-1H-1,2,4-triazole A mixture of the amine obtained in Step 9. (1.8 g) and N-cyano-1-methyl-2-(phenylmethylene)hydrazine carboximidothioic acid, methyl ether (1.3 g) is heated neat at 70° C. for 4 hours and allowed to stand at RT overnight. The residue is taken up in acetone/5% aq. HCl (10 ml:15 ml) stirred for 30 minutes, diluted with H$_2$O and extracted with ether. The aqueous phase is made basic and extracted with ethyl acetate. The ethyl acetate extract is washed with sat'd NaCl, dried, filtered and evaporated in vacuo. The residue is crystallized from ethyl acetate and recrystallized from acetonitrile and methanol affording the desired product, M.P.=185°–186° C.

EXAMPLE 9

THE PREPARATION OF 1-AMINO-2-[3-[7-[3-PIPERIDINO-2,2-DIMETHYL-2,3-DIHYDROBENZOFURANYLOXY]]-PROPYLAMINO]CYCLOBUTENE-3,4-DIONE

A solution of 7-(3-aminopropoxy)-3-piperidino-2,2-dimethylbenzofuran (0.9 g) in methanol (9.3 ml) is added dropwise to a stirred solution of 1,2-dimethoxycyclobutene-3,4-dione (0.4 g) in methanol (9.3 ml) cooled to 0° C. under nitrogen. The reaction mixture is stirred at 0° C. for 10 min. and at RT for 2½ hours. The solution is cooled to 0° C. and anhydrous ammonia gas is bubbled into the reaction mixture for 10 min. and the reaction mixture stirred under nitrogen at RT for 48 hours. The mixture is evaporated and the residue recrystallized from isopropyl alcohol affording the desired product as the hemihydrate, M.P.=230°–232° C.

EXAMPLE 10

THE PREPARATION OF 3-AMINO-5-[4-[7-[3-PIPERIDINO-2,2-DIMETHYL-BENZOFURANYLOXY]]BUTYLAMINO]-1-METHYL-1H-1,2,4-TRIAZOLE

Step 1.
7-(4-Bromobutoxy)-3-piperidino-2,2-dimethylbenzofuran

Crushed potassium hydroxide (19.6 g) and tetrabutyl ammonium chloride (1.7 g) are added to a solution of 7-hydroxy-3-piperidino-2,2-dimethylbenzofuran (14.4 g) in 1,4-dibromobutane (69.4 ml) and the mixture stirred at RT under nitrogen for 5 hours. The reaction mixture is diluted with ether, washed with water, extracted with 5% aq. HCl and the acidic phase washed with ether. The acidic phase is made basic thereby forming an oil which is taken up in ether, washed with sat'd aq. NaCl, dried, filtered and evaporated in vacuo affording the desired product as a liquid.

Step 2.
7-(4-Azobutoxy)-2,2-dimethyl-3-piperidino-2,3-dihydrobenzofuran

Sodium azide (3.35 g) is added to a stirred solution of the bromo product obtained in Step 1. (19.7 g) in a mixture of water (40 ml) and ethanol (400 ml). The reaction mixture is refluxed for 22 hours, poured into water and extracted with methylene chloride. The organic phase is washed with water, sat'd aq. NaCl, dried, filtered and evaporated in vacuo affording the desired product.

Step 3.
7-(4-Aminobutoxy)-3-piperidino-2,2-dimethyl-2,3-dihydrobenzofuran

A solution of the crude azo compound obtained in Step 2. (17.4 g) in anhydrous THF (50 ml) is added dropwise to a stirred suspension of lithium aluminum hydride (2.5 g) in anhydrous diethyl ether (520 ml) under nitrogen. The reaction mixture is refluxed for 1 hour and quenched with H$_2$O (2.5 ml), 15% aq. NaOH and H$_2$O (7.5 ml). The reaction mixture is filtered, dried, filtered and evaporated in vacuo to afford a crude product which is chromatographed on silica gel (ethyl acetate/methanol (1:1)) affording the desired product as a liquid.

Step 4.
3-Amino-5-[4-[7-[3-piperidino-2,2-dimethylbenzofuranyloxy]]butylamino]-1-methyl-1H-1,2,4-triazole A neat mixture of the butylamino compound obtained in Step 3. (1.9 g) and N-cyano-1-methyl-2-(phenylmethylene) hydrazine carboximidothioic acid, methyl ether (1.38 g) is heated to 70° C. for 4 hours. The reaction mixture is allowed to cool, dissolved in a mixture of 5% aq. HCl/acetone (3:2, 50 ml) and the aqueous solution washed with diethyl ether. The aqueous solution is made alkaline resulting in the formation of an oil which is taken up in ethyl acetate, washed with sat'd aq. NaCl, dried, filtered and evaporated in vacuo. The residue is chromatographed on silica gel (methanol/ethyl acetate (1:3)) and the purified material twice recrystallized from acetonitrile affording the desired product, M.P.=158°–159° C.

EXAMPLE 11

THE PREPARATION OF 1-AMINO-2-[4-[7-[3-PIPERIDINO-2,2-DIMETHYL-2,3-DIHYDROBENZOFURANYLOXY]]-BUTYLAMINO]CYCLOBUTENE-3,4-DIONE

A solution of 7-(4-aminobutoxy)-3-piperidino-2,2-dimethyl-2,3-dihydrobenzofuran (2.3 g) in methanol (23 ml) is added dropwise to a solution cooled to 0° C. of 1,2-dimethoxycyclobutene-3,4-dione (1.04 g) in methanol (23 ml). The reaction mixture is stirred for 20 minutes at 0° C. and 2½ hours at RT. The solution is cooled to 0° C. and anhydrous ammonia gas bubbled into the solution for 10 minutes after which the solution is stirred under nitrogen overnight at ambient temperature. The reaction mixture is filtered, the filtered solid washed with cold methanol and ether and air dried. The dried solid and the evaporated filtrate residue are recrystallized from isopropanol, and recrystallized from methanol affording the desired product, M.P.=213°-215° C.

EXAMPLE 12

THE PREPARATION OF 3-AMINO-4-[4-[7-[3-PIPERIDINO-2,2-DIMETHYL-2,3-DIHYDROBENZOFURANYLOXY]]-BUTYLAMINO]-1,2,5-THIADIAZOLE MONOOXIDE

A solution of 7-(4-aminobutoxy)-3-piperidino-2,2-dimethyl-2,3-dihydrobenzofuran (2.5 g) in methanol (31 ml) is added dropwise to a stirred solution cooled to less than 3° C. of 3,4-dimethoxy-1,2,5-thiadiazole monooxide (1.27 g) in methanol (140 ml) under nitrogen. The reaction mixture is stirred at low temperature for 3 hours after which anhydrous ammonia gas is bubbled through the solution for 10 minutes and the solution stirred at RT overnight. The reaction mixture is evaporated and the residue twice recrystallized from methanol affording the desired product, M.P.=188°-190° C.

EXAMPLE 13

THE PREPARATION OF 3-HYDROXYMETHYL-5-[4-[7-(2,2-DIMETHYL-3-PIPERIDINO-2,3-DIHYDROBEN-ZOFURANYLOXY)]BUTYLAMINO]-1-METHYL-1H-1,2,4-TRIAZOLE

Step 1.

1-Acetoxyacetyl-2-methyl-2-[phenylmethleneamino]-3-4-[7-(2,2-dimethyl-3-piperidino-2,3-dihydroben-zofuranyloxy)butyl]guanadine A neat mixture of methyl-N-[2-(acetyloxy)acetyl]-1-methyl-2-(phenylmethylene)hydrazine carboximidiothioate (6.7 g) and 7-(4-aminobutoxy)-4-piperidino-2,2-dimethyl-2,3-dihydrobenzofuran (6.0 g) is heated to 65° C. for 18 hours under vacuum. Boiling ethyl acetate (70 ml) is added to the heated mixture and the mixture is stirred. The mixture is allowed to cool thereby forming a precipitate which is filtered and the filtrate is concentrated in vacuo. The residue is triturated with ether forming a precipitate which is filtered. The filtrate is concentrated in vacuo yielding the desired product as an oil which is used in the next step without further purification.

Step 2.

3-Hydroxymethyl-5-[4-[7-(2,2-dimethyl-3-piperidino-2,3-dihydrobenzofuranyloxy)]butylamino]-butylamino]-1-methyl-1H-1,2,4-triazole A mixture of the guanadine obtained in Step 1. (11.94 g), aqueous HCl (2N, 250 ml) and absolute ethanol (40 ml) is stirred at RT for about 20 hours. The reaction mixture is washed with ether and the aqueous portion is neutralized with potassium carbonate. A solution of 4M KOH (15.5 ml) and absolute ethanol (40 ml) are added to the mixture and stirring is continued for 1½ hours. The aqueous mixture is concentrated, extracted with ethyl acetate and the organic extract dried, filtered and concentrated in vacuo. The residue is covered with ether forming a solid which is filtered, dissolved in warm methanol and chromatographed on silica gel (methanol). The purified fractions were combined and concentrated forming an oil which is triturated with ether. The resulting solid is recrystallized from hot ethyl acetate and the crystalline material dissolved in methanol, chromatographed (methanol) and the purified fractions combined and concentrated in vacuo to an oil which is triturated affording the desired product as the ¼ hydrate, M.P.=135°-137° C.

Utilizing starting materials and reaction conditions analogous to those described above, 3-amino-4-[3-[6-[4-(1-piperidinyl)]-2,3-dihydrobenzopyranyloxy]-propylamino]]-1,2,5-thiadiazole monoxide, M.P.=197°-199° C., and the compounds disclosed in Tables I and II below are prepared.

TABLE I

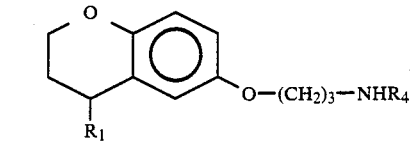

| $R_1$ | $R_4$ |
|---|---|
| 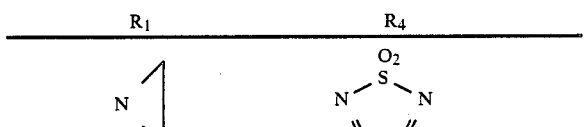 | |
| 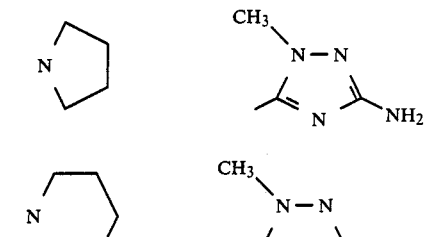 | |
| 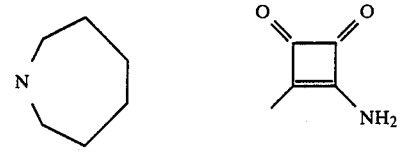 | |
| 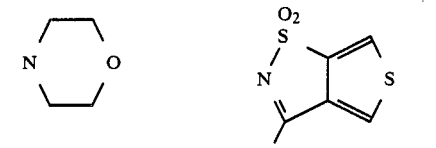 | |
| 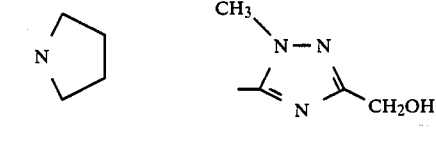 | |
| 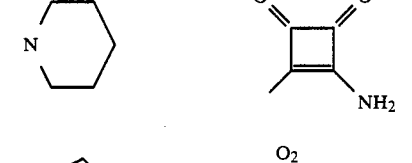 | |
|  | |

TABLE I-continued

| R₁ | R₄ |
|---|---|
| morpholino | 4-amino-1,2,5-thiadiazole-3-methyl 1,1-dioxide |
| thiomorpholino | 3-amino-1-methyl-5-methyl-1,2,4-triazole |
| aziridinyl | 3-(hydroxymethyl)-1-methyl-5-methyl-1,2,4-triazole |
| pyrrolidinyl | 2-amino-3-methylcyclobutenedione |
| piperidinyl | thieno-isothiazole dioxide |
| hexamethyleneimino | 4-amino-1,2,5-thiadiazole-3-methyl 1,1-dioxide |
| morpholino | 3-amino-1-methyl-5-methyl-1,2,4-triazole |
| thiomorpholino | 3-(hydroxymethyl)-1-methyl-5-methyl-1,2,4-triazole |
| aziridinyl | 2-amino-3-methylcyclobutenedione |
| piperidinyl | thieno-isothiazole dioxide |

TABLE II

| R₁ | R₄ |
|---|---|
| aziridinyl | 4-amino-1,2,5-thiadiazole-3-methyl 1,1-dioxide |
| pyrrolidinyl | 3-amino-1-methyl-5-methyl-1,2,4-triazole |
| piperidinyl | 3-(hydroxymethyl)-1-methyl-5-methyl-1,2,4-triazole |
| hexamethyleneimino | 2-amino-3-methylcyclobutenedione |
| morpholino | thieno-isothiazole dioxide |
| pyrrolidinyl | 3-(hydroxymethyl)-1-methyl-5-methyl-1,2,4-triazole |
| piperidinyl | 2-amino-3-methylcyclobutenedione |

TABLE II-continued

Structure: chroman with O—(CH$_2$)$_3$—NHR$_4$ at position 8 and R$_1$ at position 4

| R$_1$ | R$_4$ |
|---|---|
| azepane (N-7-membered ring) | thieno-isothiazole-dioxide (O$_2$S-N=) |
| morpholine (N—O 6-ring) | 1,2,5-thiadiazole-1,1-dioxide with NH$_2$ |
| thiomorpholine (N—S 6-ring) | 1-methyl-5-amino-1,2,4-triazole (CH$_3$-N-N, N, NH$_2$) |
| azetidine | 1-methyl-5-hydroxymethyl-1,2,4-triazole (CH$_3$-N-N, N, CH$_2$OH) |
| pyrrolidine | 3-amino-4-methyl-cyclobutene-1,2-dione (squarate, NH$_2$) |
| piperidine | thieno-isothiazole-dioxide |
| azepane | 1,2,5-thiadiazole-1,1-dioxide with NH$_2$ |
| morpholine | 1-methyl-5-amino-1,2,4-triazole |
| thiomorpholine | 1-methyl-5-hydroxymethyl-1,2,4-triazole |
| azetidine | 3-amino-4-methyl-squarate (NH$_2$) |
| piperidine | thieno-isothiazole-dioxide |
| azepane | 1,2,5-thiadiazole-1,1-dioxide with NH$_2$ |

Various tests in animals have been carried out to show the ability of the compounds of this invention to exhibit pharmacological responses that can be correlated with activity in humans. These tests involve such factors as the effect of the compounds of Formula I on gastric secretion and their H$_2$ antagonist, anti-ulcer and cytoprotective activity. It has been found that the compounds of this invention when tested in the above variety of situations show a marked activity.

One such test is the gastric secretion test. This test is carried out as follows: Shay rats are fasted for 4-8 hours, and water is given ad lib. The rats are selected at random and separated into groups of 10. The animals are treated intraduodenally (I.D.) with the test compounds or the vehicle immediately subsequent to the ligation of the stomach at the pyloric sphincter. The animals are sacrificed with chloroform at 4 hours post-drug administration, the stomach removed and its contents assayed for volume, pH and total acids.

A second gastric secretion test is carried out on the dog. This is outlined in the *Handbook of Physiology*, Section 6: Alimentary Canal, Volume II: Secretion. American Physiology Society, Washington, D.C., 1967.

It has been found that the compounds of this invention, when subjected to the above gastric secretion tests, display marked ability to decrease gastric volume and gastric acidity. These tests are known to correlate well with gastric activity in humans and are standard tests used to determine anti-secretory properties.

The compounds of Formula I have been found to be histamine H$_2$-receptor antagonists by the results obtained in the following H$_2$-antagonist tests.

A. Isolated Guinea Pig Atria

The H$_2$-receptor antagonist activity of the compounds of Formula I is measured by observing the beat rate response versus compound concentration in isolated guinea pig atria. A discussion of criteria to evaluate these dose-response curves may be found in, E. J. Ariens, G. A. J. vanOs, A. M. Simonis, and T. M. van Rossum, "A Molecular Approach to General Pharmacology", Sections 11A, 11B, and 11!. *Molecular Phar-*

*macology: The Mode of Action of Biologically Active Compound.* Vol. 1, Academic Press (1964).

1. Tissue Bath

A fifty ml jacketed tissue bath is maintained at 30° C. The bath consists of a Krebs-Henseleit buffer aerated with 95% $O_2$–5% $CO_2$, (pH 7.4). The buffer is prepared by mixing: 4 ml of an aqueous (distilled deionized) solution of $CaCl_2.2H_2O$ (0.37 g/ml); 4 ml of an aqueous (distilled deionized) solution of $MgSO_4.7H_2O$ (0.29 g/ml); 7.2 g of glucose; and, 2 liters of aqueous (distilled deionized) solution containing NaCl (28 g), $NaHCO_2$ (8.4 g), KCl (1.4 g) and $KH_2PO_4$ (0.6 g).

2. Preparation of Atria

Male albino guinea pigs (400–700 g, preferably 500–600 g) are killed by a blow to the back of the head and exsanguinated by cutting jugular veins and carotid arteries. The thoracic skin is opened from this neck cut and the rib cage exposed. Both sides of the rib cage and the diaphragm are cut and laid back, exposing the heart. The heart is removed by cutting through the vessels above and behind it while it is slightly elevated with forceps holding the ventricle tip. The heart is immediately placed in warm, aerated buffer and further dissected in a large petri dish of the same buffer. Since the pericardium is removed, it is possible to slip iris scissors between the atria and ventricles while holding the aorta and vessels with tweezers and cut off the atria. The atria are then dissected from any remaining tissue and vessels and suspended in the bath using small, curved taper-point needles formed into hooks and tied to an S-shaped hook and the L-shaped lower support with 00 silk.

A Beckman Type 9308 Strain Gauge Coupler connects a Beckman cardiotachometer to a Grass FT03C strain gauge supported in a rack and pinion clamp. The upper hook of the strain gauge is placed in the edge of the left atrium and the lower hook in the tip of the right atrium. The lower support is clamped in a femur clamp and the upper hook is suspended from the strain gauge lug. The strain gauge is raised until the resting tension on the tissue is 1 gram. The tissue is allowed to stabilize for about one hour with several buffer washings and tension adjustments before the addition of the test compounds.

3. Test Procedure

A control dose-response curve using cumulative, approximately tripling doses is obtained in all three running from 0.1 to 30.0 $\mu$M histamine (0.1, 0.3, 1.0, 3.0, etc.). In order to minimize volume changes when adding drugs to the bath, small volumes of concentrated solutions are used. It is convenient to make up a 0.5M solution and dilute it to give 50, 5 and 0.5 mM solutions.

Data recorded consists of the initial baseline rate and the stable plateau rate after each addition. Histamine is then washed out and the tissues are allowed to stabilize again near the initial baseline rate; this may take several rinses and 1 hr. The test compound is then added at the same cumulative doses and rates again recorded. If the compound behaves as an agonist and stimulates, then the dose is increased until the rate plateaus or the concentrtion is 1.0 mM. If, however, no agonist activity is observed when the concentrations has reached 100 $\mu$M then its antagonistic activity is assessed by repeating the histamine curve without washing out the test compound. Reversibility of effect is assessed by attempting to wash out the test compound and/or histamine and repeat the histamine curve. Erratic or irregular beating or any other abnormal behavior at any time is noted. Calculations consist of the change in rate from base line and that change as a percentage of the maximum rate obtained in the initial control curve. The mean of those percentages ($\pm$SEM) is plotted as a function of agonist concentration (either histamine or test compound) to evaluate the type of response.

B. Lumen Perfused Rat Stomach—Effect on the Gastric Secretion

Male Sprague-Dawley rats weighing between 350 and 500 gm are housed individually according to standard animal husbandry procedures and are deprived of food twenty-four hours prior to testing. The rats are anesthetized by an intraperitoneal injection of 25% solution of urethane (0.5 to 0.7 ml/100 g of body weight). Once anesthetized, the trachea is exposed and cannulated with PE 100 tubing. The jugular vein is exposed and cannulated with PE 50 tubing bevelled at the tip. The abdomen is opened through a midline incision, and the esophagus is isolated excluding the vagus nerve. PE 190 tubing, with a flange on one end, is passed down the rat's mouth through the esophagus and into the stomach. The esophagus is tied off and the tubing checked to make sure that it is securely in the stomach. The duodenum is then identified and a small cut made about 1 cm below the pyloric sphincter. A piece of PE 320 tubing (flanged at one end) is inserted through the cut and into the stomach. It is secured firmly by tying a ligature around the pylorus. Using a 50 ml syringe, the stomach is flushed out with 0.4 mM NaOH through the esophageal tube until the perfusate emerging from the pyloric tube is clear. The animal is placed on a tilted table covered with a Gordon-Rupp water blanket Model 'K' to maintain the rat's body temperature at 30° C. The tube going into the esophagus is attached to a Sage Peristaltic Pump and 0.4 mM NaOH (pH 10.0) is perfused and collected in 30 ml beakers. The beakers are changed every 10 or 15 minutes and the pH of these samples are recorded. Once the pH has stabilized around 6.5–7.5, drugs that affect gastric secretion are given intravenously. The effectiveness of a compound is based on its ability to prevent a drop in pH initiated by a gastric stimulant, such as histamine. See, Ghosh, M. N. and Schild, H. O., *Brit. J. Pharmacol.*, 13: 54 (1958).

Compounds within the scope of Formula I have also been determined to exhibit anti-ulcer activity. The anti-ulcer properties of these compounds can be evaluated using an anti-ulcer assay in which aspirin or another nonsteroidal anti-inflammatory agent is used to induce gastric ulcers in the rat according to the following test procedure.

See, Corell, T., "Interaction of Salicylates and other Non-steroidal Anti-inflammatory Agents in Rats as Shown by Gastro-ulcerogenic and Anti-inflammatory Activities, and Plasma Concentrations", Acta. Pharmacology et. Toxicology, 45, 225–231 (1979).

Male Sprague-Dawley rats 140–170 g are housed according to standard animal husbandry procedures. The rats are fasted twenty-four hours prior to testing. On the test day, rats are divided into groups of 5 to 10, with one group serving as controls and receiving vehicle (for example, distilled water or a 0.1% Tween 80 solution). The test compounds, using logarithmic doses, are administered at a dose volume of 10 ml/kg. Thirty minutes post-drug, the rats are orally administered (10 ml/kg) aspirin or indomethacin suspended in 0.1% Tween 80 at a dose of 150.0 or 20.0 mg/kg, respectively. Four hours following indomethacin administration (five hours after aspirin administration) animals are sacrificed via cervical dislocation; their stomachs are removed, opened along the greater curvature, and gently rinsed and examined for lesions with a 10X magnifying glass; the following scale is employed:

| Grade | Description |
| --- | --- |
| 0 | No lesions |
| 1 | 5 lesions, all < 2 mm |
| 2 | 5 lesions, at least 1 > 2 mm |
| 3 | 5-10 lesions, all < 2 mm |
| 4 | 5-10 lesions, at least 1 > 2 mm |
| 5 | 10 lesions, all < 2 mm |
| 6 | 10 lesions, at least 1 > 2 mm |
| 7 | Perforation |

The average ulcer severity ($\pm$S.E.) for each group of animals is calculated. The percent inhibition for each test compound is calculated as follows:

$$\% \text{ inhibition} = \frac{\text{Mean value for control} - \text{Mean value for experimental}}{\text{Mean value for control}} \times 100$$

The compounds of Formula I have also been determined to exhibit cytoprotective activity.

The cytoprotective effectiveness of the compounds of Formula I is evaluated according to the following test procedure.

Male Sprague-Dawley rats 150-200 g are housed according to standard animal husbandry procedures. The rats are fasted twenty-four hours prior to testing. On the test day, rats are divided into groups of 6, with one group serving as controls and receiving vehicle (for example, distilled water or a 0.5% Methocel solution). The test compounds, using logarithmically spaced doses, are administered at a dose volume of 5 ml/kg. Ten minutes post-drug, the rats are orally administered 1 ml of absolute alcohol, 0.2N NaOH (1 ml) or 0.6N HCl (1 ml), regardless of body weight. One hour after administration animals are sacrificed by cervical dislocation, their stomachs are removed, opened along the greater curvature, rinsed under running tap water and examined for lesions with a 2X-10X magnifying glass.

The reduction of lesion count, lesion severity score and ulcer index as compared to similar measurements made in the controls was expressed as a percentage. Measurement of statistical significance of the results was done by standard methods.

The average ulcer severity ($\pm$S.E.) for each group of animals is calculated. The percent inhibition for each test compound is calculated as follows:

$$\% \text{ inhibition} = \frac{\text{Mean value for control} - \text{Mean value for experimental}}{\text{Mean value for control}} \times 100$$

The results of the anti-secretory, anti-ulcer and cytoprotective assays, detailed above, establish the utility of the compounds of the present invention in the treatment of peptic ulcers in mammals, including humans. These compounds both aid in the healing of such ulcers and also prevent their formation.

The most preferred $H_2$-antagonist compounds are compounds within the scope of Formula I wherein Z is $NHR_4$ and $R_4$ is 2-[1-amino-cyclobutene-3,4-dione].

In particular, the compounds according to Formula I are useful: in the treatment and prevention of of hyperacidity and gastrointestinal ulceration; for decreasing gastrointestinal acid secretion in mammals; and for enhancing the gastrointestinal resistance to gastrointestinal irritants in humans and other mammals.

For all these purposes, the compounds of this invention can be normally administered orally or parenterally. Oral administration is preferred.

Compounds within the scope of Formula I are readily absorbed in the gastrointestinal system and exhibit excellent oral activity and a duration of action which is on the order of about 4 to about 24 hours, preferably about 8 to about 12 hours.

The compounds according to the invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients, for example, $H_1$-antagonists, or known antacids such as aluminum hydroxide, magnesium hydroxide, magnesium trisilicate, aluminum glycinate, or calcium carbonate. Suitable carriers include diluents or fillers, sterile aqueous media and various non-toxic organic solvents. The compositions may be formulated in the form of tablets, capsules, lozenges, troches, hard candies powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, are also useful for intravenous injection purposes, provided that their pH is properly adjusted, suitably buffered, and made isotonic with sufficient or glucose.

The dosage regimen in carrying out the methods of this invention is that which insures maximum therapeutic response until improvement is obtained and thereafter the minimum effective level which gives relief. Thus, in general, the dosages are those that are therapeutically effective in the treatment of gastrointestinal disease conditions or symptoms, such as duodenal and peptic ulcer. In general, the dose can be between about 0.1 mg/kg and 100 mg/kg (preferably in the range of 1 to 20 mg/kg), bearing in mind, of course, that in selecting the appropriate dosage in any specific case, consideration must be given to the patient's weight, general health, age, and other factors which may influence response to the drug. The daily dose can range from 1 to 4 times a day, and can be 1 to about 3 to 1 to about 2 times a day depending on the specific compound and its duration of action.

We claim:

1. A compound of the formula:

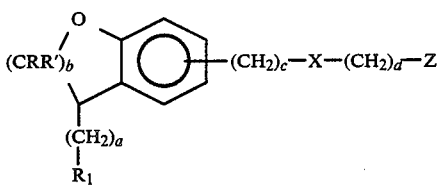

wherein:
a is 0, 1 or 2;
b is 1 or 2;
c is 0 or 1;
d is 2, 3 or 4;
X is oxygen, sulfur,

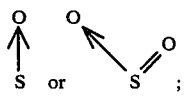

Z is —$NHR_4$,
R and R' are each independently H or alkyl;
$R_1$ is —$NR_2R_3$
$R_2$ and $R_3$ are each independently H or alkyl, or both together are alkylene or alkylidinyl and with the nitrogen to which they are attached form a 5, 6, or 7-membered ring which may include one to three additional hetero atoms of N, O or S;
$R_4$ is

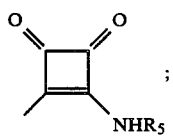

$R_5$ is H or lower alkyl;
or a pharmaceutically acceptable salt thereof.

2. A compound according to claim 1 wherein:
a is 0;
b is 1;
d is 3; and
X is oxygen.

3. A compound of the formula

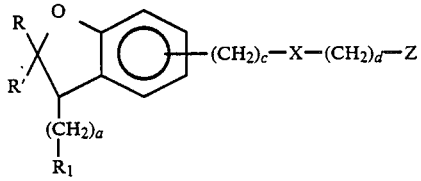

wherein:
a is 0, 1 or 2;
c is 0 or 1;
d is 2, 3 or 4;
R and R' are each independently H or lower alkyl;
X is oxygen or sulfur;
Z is —$NHR_4$
$R_1$ is —$NR_2R_3$;
$R_2$ and $R_3$ are each independently H or alkyl, or both together are alkenyl or alkylidinyl with the nitrogen to which they are attached form a 5, 6 or 7-membered ring heterocycle which may include one to three additional hetero atoms of N, O or S;
$R_4$ is

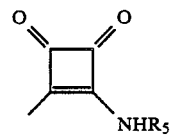

$R_5$ is H or lower alkyl;
or a pharmaceutically acceptable salt thereof.

4. A compound according to claim 3 of the formula:

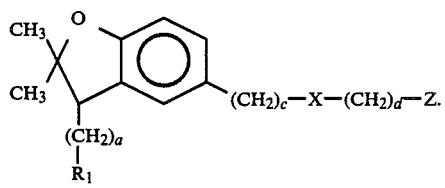

5. A compound according to claim 3 of the formula:

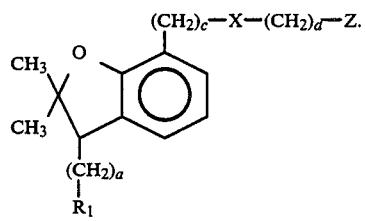

6. A compound of the formula:

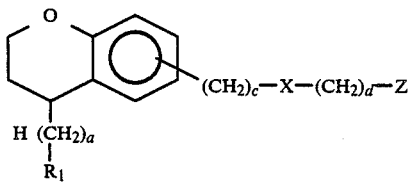

wherein:

a is 0, 1 or 2;
c is 0 or 1;
d is 2, 3 or 4;
X is oxygen or sulfur;
Z is —NHR$_4$
R$_1$ is —NR$_2$R$_3$;
R$_2$ and R$_3$ are each independently H or alkyl, or both together alkenyl or alkylidinyl and with the nitrogen to which they are attached form a 5, 6 or 7-membered ring heterocycle which may include one to three additional hetero atoms of N, O or S;
R$_4$ is

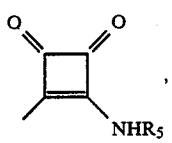

R$_5$ is H or lower alkyl;
or a pharmaceutically acceptable salt thereof.

7. A compound according to claim 6 wherein:
a and c are 0;
d is 3; and
X is oxygen.

8. A compound according to claim 6 wherein:
a is 0;
c is 1;
d is 2; and
X is sulfur.

9. A compound of the formula:

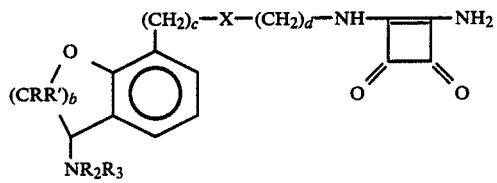

wherein:
b is 1 or 2;
c is 0 or 1;
d is 2, 3, or 4;
X is oxygen or sulfur;
R and R' are each independently H or lower alkyl;
R$_2$ and R$_3$ are together alkylene or alkylidinyl and with the nitrogen to which they are attached form a 5, 6 or 7 membered heterocyclic ring which may include one to three additional hetero atoms of N, O or S; or a pharmaceutically acceptable salt thereof.

10. A compound according to claim 9 wherein:
R$_1$ is 1-piperidinyl, 1-pyrrolidinyl, 1-morpholinyl or 1-azepinyl.

11. A compound according to claim 1, which is 1-Amino-2-[3-[8-[4-(1-piperidinyl)-2,3-dihydrobenzopyranyloxy]]propylamino]-cyclobutene-3,4-dione or a pharmaceutically acceptable salt thereof.

12. A compound according to claim 1, which is 1-Amino-2-[3-[6-[4-(1-piperidinyl)-2,3-dihydrobenzopyranyloxy]]propylamino]-cyclobutene-3,4-dione or a pharmaceutically acceptable salt thereof.

13. A compound according to claim 1, which is 1-Amino-2-[3-[7-[3-(1-piperidinyl)-2,2-dimethyl-2,3-dihydrobenzofuranyloxy]]propylamino]-cyclobutene-3,4-dione or a pharmaceutically acceptable salt thereof.

14. A compound according to claim 1, which is 1-Amino-2-[4-[7-[3-(1-piperidinyl)-2,2-dimethyl-2,3-dihydrobenzofuranyloxy]]butylamino]-cyclobutene-3,4-dione or a pharmaceutically acceptable salt thereof.

15. A compound according to claim 1, wherein the carbon atom to which the R$_1$—(CH$_2$)$_a$— group is attached is in the S configuration.

16. A compound according to claim 5, which is the S(+) enantiomeric base or a pharmaceutically acceptable salt thereof.

17. A compound according to claim 6, which is the S(+) enantiomeric base or a pharmaceutically acceptable salt thereof.

18. A compound according to claim 9, which is the S(+) enantiomeric base or a pharmaceutically acceptable salt thereof.

19. A compound according to claim 1, wherein the carbon atom to which the R$_1$—(CH$_2$)$_a$— group is attached is in the R— configuration.

20. A compound according to claim 1, which is the racemic mixture of the base or a pharmaceutically acceptable salt thereof.

21. A pharmaceutical composition wherein the active ingredient is a compound according to claim 1 in admixture with a pharmaceutical carrier.

22. A method for decreasing acid secretion in the gastrointestinal tract of mammals by administering thereto an anti-secretory effective amount of a compound according to claim 1.

23. A method for the treatment of gastrointestinal hyperacidity and ulceration in a mammal comprising administering thereto an effective amount of a compound according to claim 1.

24. A method for enhancing the gastrointestinal resistance to gastrointestinal irritants in humans and mammals comprising administering thereto an effective cytoprotective amount of a compound of the formula according to claim 1.

* * * * *